(12) United States Patent
Albers et al.

(10) Patent No.: US 8,309,075 B2
(45) Date of Patent: Nov. 13, 2012

(54) EDIBLE PRODUCT CONTAINING GINSENG POLYSACCHARIDES AND BENEFICIAL BACTERIA

(75) Inventors: Ruud Albers, Vlaardingen (NL); Wilhelmina Martina Blom, Vlaardingen (NL); Adrianus Marinus Ledeboer, Vlaardigen (NL); Ingrid Celestina Mohede, Vlaardingen (NL); Jan Willem Sanders, Vlaardingen (NL)

(73) Assignee: Nutrileads, Rockanje (NL)

( * ) Notice: Subject to any disclaimer, the term of this patent is extended or adjusted under 35 U.S.C. 154(b) by 1100 days.

(21) Appl. No.: 12/084,854

(22) PCT Filed: Oct. 26, 2006

(86) PCT No.: PCT/EP2006/010324
§ 371 (c)(1),
(2), (4) Date: May 12, 2008

(87) PCT Pub. No.: WO2007/054208
PCT Pub. Date: May 18, 2007

(65) Prior Publication Data
US 2009/0269307 A1    Oct. 29, 2009

(30) Foreign Application Priority Data
Nov. 14, 2005 (EP) .................................. 05077592

(51) Int. Cl.
| | |
|---|---|
| *A23B 7/148* | (2006.01) |
| *A23C 17/00* | (2006.01) |
| *A21D 13/00* | (2006.01) |
| *A01N 63/00* | (2006.01) |
| *A01N 65/00* | (2009.01) |
| *A61K 36/254* | (2006.01) |
| *B65D 85/00* | (2006.01) |
| *C08B 37/00* | (2006.01) |

(52) U.S. Cl. .................... 424/93.45; 424/93.4; 424/728; 426/43; 426/106; 426/138; 426/531; 426/590

(58) Field of Classification Search ........................ None
See application file for complete search history.

(56) References Cited

U.S. PATENT DOCUMENTS
6,098,795 A * 8/2000 Mollstam et al. ............. 206/222
6,432,454 B1   8/2002 Shan et al.
2005/0074440 A1  4/2005 Lin FOREIGN PATENT DOCUMENTS
JP     2005-160373   *  6/2005
WO    WO 03/071883 A1    9/2003

OTHER PUBLICATIONS

Kim et al., "Effect of extracting conditions on chemical compositions of Korean mountain ginseng extract", Database FSTA (online), International Food Information Service, Frankfurt-Main, DE, 2005, XP002363717.
International Search Report International Application No. PCT/EP2006/010324 dated Dec. 12, 2006.
Ouwehand et al., "The Health Effects of Cultured Milk Products with Viable and Non-viable Bacteria", International Dairy Journal 8 (1998), pp. 749-758.
Blaut et al., "Transformation of Flavonoids by Intestinal Microorganisms", Int. J. Vitam. Nutr. Res., 73 (2), 2003, pp. 79-87.
Rechner et al., "Colonic Metabolism of Dietary Polyphenols: Influence of Structure on Microbial Fermentation Products", Free Radical Biology & Medicine, vol. 36, No. 2, 2004, pp. 212-225.
Dubois et al., "Colorimetric Method for Determination of Sugars and Related Substances", Anal. Chem. 28:350-356, 1956.

* cited by examiner

*Primary Examiner* — Debbie K Ware
(74) *Attorney, Agent, or Firm* — Gilberto M. Villacorta; Sunit Talapatra; Foley & Lardner LLP

(57) ABSTRACT

One aspect of the present invention relates to an edible product containing: • probiotic bacteria in an amount of at least $10^3$ bacteria per gram; and • at least 0.5 mg/g of ginseng polysaccharides containing at least 2 monosaccharide units, preferably at least 4 monosaccharide units. Another aspect of the invention relates to the use of the aforementioned product in therapeutic and prophylactic treatments. The present invention further provides a method of producing a packaged liquid edible product containing probiotic bacteria and ginseng polysaccharides in the aforementioned amounts.

12 Claims, 2 Drawing Sheets

EDIBLE PRODUCT CONTAINING GINSENG POLYSACCHARIDES AND BENEFICIAL BACTERIA

CROSS-REFERENCE TO RELATED APPLICATIONS

Figure 1:
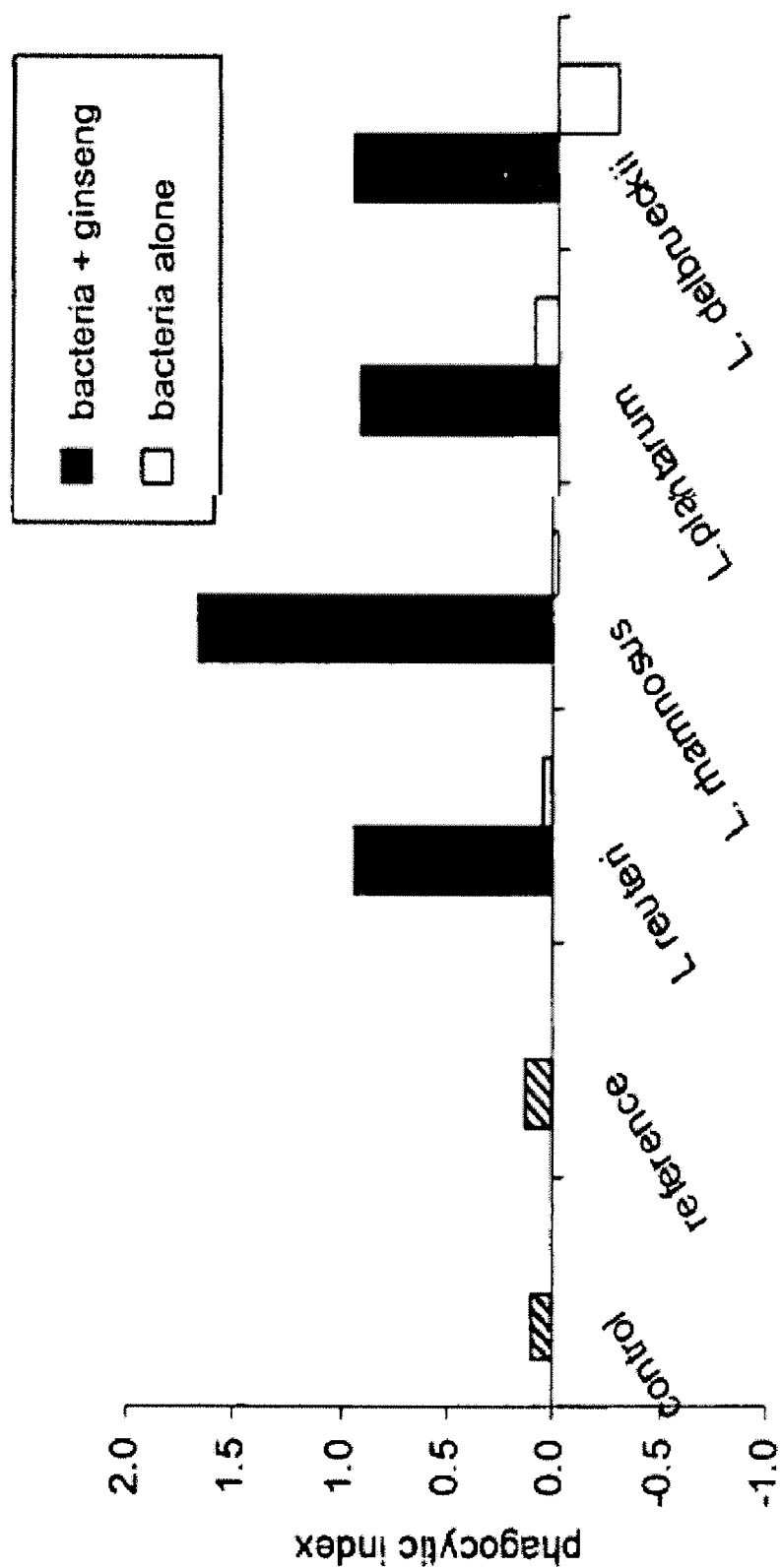

The present application is a 35 U.S.C. 371 national stage entry of PCT International Application No. PCT/EP2006/010324 filed on Oct. 26, 2006, claiming benefit of foreign priority to European Patent Application No. EP 05077592 filed on Nov. 14, 2005, both of which disclosures are hereby expressly incorporated herein in their entirety by reference.

FIELD OF INVENTION

The present invention relates to edible products comprising ginseng polysaccharides in combination with bacteria which, upon ingestion in suitable amounts, provide a health benefit.

BACKGROUND OF THE INVENTION

Hot water extracts of the Ginseng plant have traditionally (more than 2000 years) been employed as tonic to enhance resistance to infections and to improve physical and mental performance in South-East Asia. Only in recent years have rigorous scientific methods been applied to test their efficacy demonstrating large differences between different preparations. It has been argued that claims should thus only be supported by evidence obtained with a particularly standardized extract. The commonly claimed effects on mood and general wellbeing are ascribed to so-called ginsenosides.

The application of probiotic bacteria in food products is often associated with health effects, see for example A.C. Ouwehand et al. in Int. Dairy Journal 8 (1998) 749-758. In particular the application of probiotic bacteria is associated with health effects for example relating to the gut well-being such as IBS (Irritable Bowel Syndrome), IBD (inflammatory bowel diseases), reduction of lactose maldigestion, clinical symptoms of diarrhea, immune stimulation, anti-tumor activity and enhancement of mineral uptake. It is generally believed that some of the health effects of probiotic bacteria are related to their immunomodulatory and anti-inflammatory properties at mucosal sites. These health effects are most likely initiated by effects of the probiotic bacteria on the mucosal immune system in the ileum and jejunum. Said modulatory effects of probiotic bacteria have been demonstrated to beneficially affect e.g. resistance to infections, allergic diseases and inflammatory bowel diseases.

SUMMARY OF THE INVENTION

Most adults suffer two to five colds per year, and infants and pre-school children have an average of four to eight. The upper respiratory tract (URT) infections, like common colds and flu, are together with gastro-intestinal (GI) infections the most important reasons of absenteeism at work or school. In a lifetime of 75 years, we suffer from over 200 episodes of common cold. This means that if each cold lasts for five to seven days we spend around three years of our life coughing and sneezing with colds. The need and interest of a consumer in "self prevention" and "self treatment" of these acute infections are therefore high.

The inventors have discovered that the incidence of URT- and GI-infections may be reduced in a surprisingly effective manner by repeated, e.g. daily consumption of an edible product containing high levels of ginseng polysaccharides in combination with high concentrations of probiotic bacteria. More particularly, the inventors have found that these health benefits may be achieved by providing an edible product containing:

probiotic bacteria in an amount of at least $10^3$ bacteria per gram; and at least 0.5 mg/g of ginseng polysaccharides.

Although the inventors do not wish to be bound by theory, it is believed that in the gut the microbial metabolism of the probiotic bacteria yields biologically active metabolites of the ginseng polysaccharides that provide surprisingly effective protection against gastrointestinal and respiratory infections. The beneficial effects observed for the edible products of the present invention may also (partially) be caused by metabolisation of biologically active components that have an adverse effect on a subject's resistance against the aforementioned infections.

Many natural sources of biologically active components need to be metabolised by the commensal intestinal flora in order to release the biologically active components contained therein and to allow these biologically active components to exert their effects on the body of the host [Blaut et al., Int J Vitam Nutr Res. 2003 March;73 (2):79-87). It is also known that the intestinal microflora is highly variable between subjects and is influenced by age, diet, use of medication, disease state and other yet unknown factors. This makes the bioavailability of relevant bioactive components (from food and beverages) in any given subject highly unpredictable (Rechner et al., Free Radic Biol Med. 2004 Jan. 15;36(2):212-25).

The present invention provides an edible product that contains ginseng polysaccharides in combination with probiotic bacteria whose microbial metabolism are capable of modulating certain bioactive components contained in the ginseng, notably ginseng polysaccharides. Thus, the present product effectively maximises bioavailability of the beneficial bioactive components contained in ginseng and/or reduces the effect of bioactive components with an adverse effect. Furthermore, performance of the present product is hardly affected by factors such as age, diet, medication etc.

BRIEF DESCRIPTIONS OF THE DRAWINGS

Figure 2:
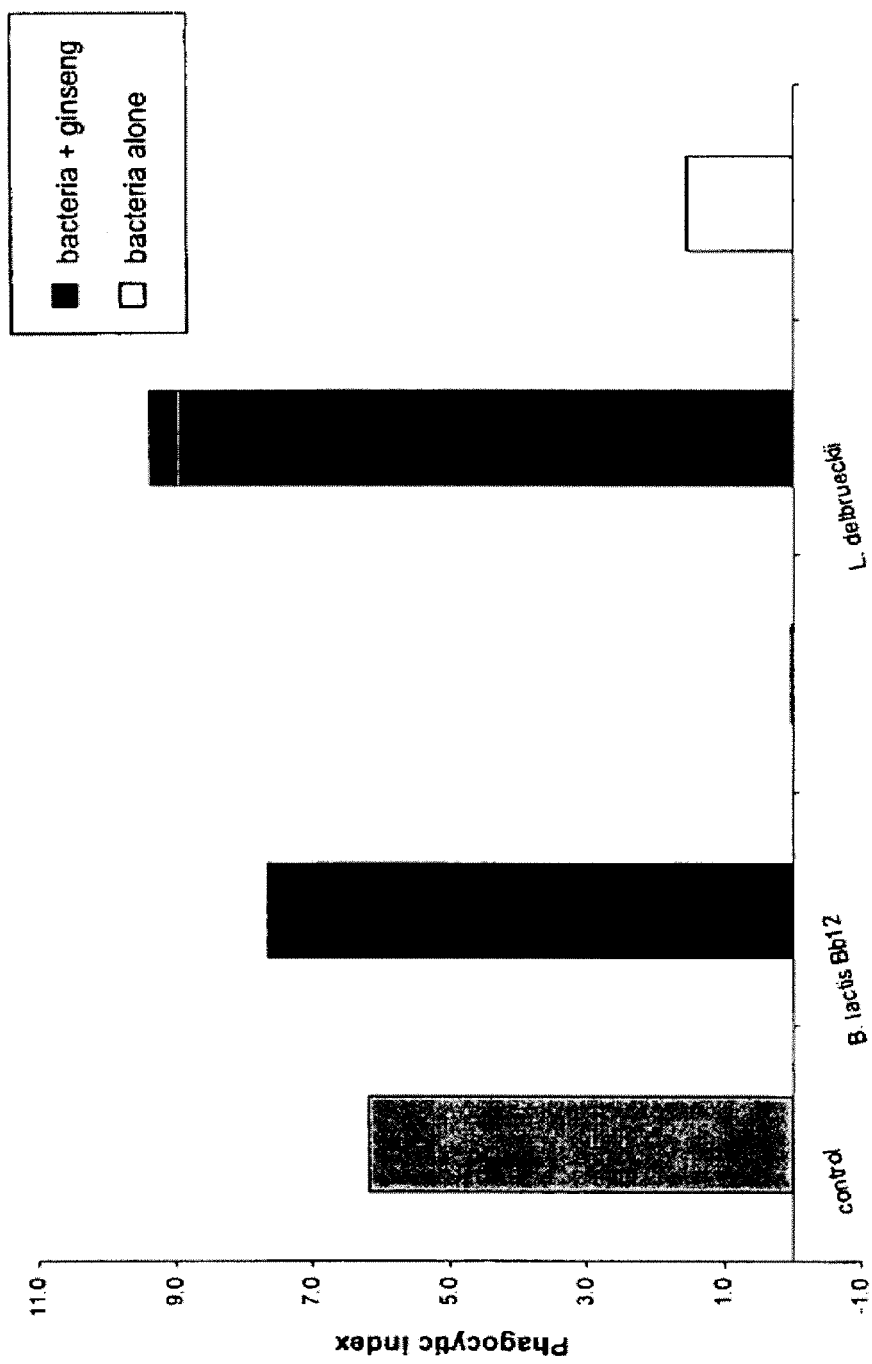

FIG. 1 shows the phagocytic index for cells.
FIG. 2 shows the phagocytic index and for cells.

DETAILED DESCRIPTION OF THE INVENTION

Accordingly, one aspect of the present invention relates to an edible product containing:

probiotic bacteria in an amount of at least $10^3$ bacteria per gram; and at least 0.5 mg/g of ginseng polysaccharides containing at least 2 monosaccharide units, preferably at least 4 monosaccharide units.

As used herein the term "fat" encompasses fatty acid esters, notably triglycerides, diglycerides, monoglycerides, phospholipids and combinations thereof. The fat may be solid or liquid under ambient conditions.

The term "probiotic bacteria" or "probiotics" as used herein, refers to microorganisms which when administered in adequate amounts confer a health benefit to the consumer. The probiotics according to the invention may be viable or non-viable. In case the probiotics are non-viable, they have to be substantially structurally intact, meaning that these non-viable micro-organisms are still sufficiently intact to avoid or delay disintegration in the distal intestinal tract thereby enabling the interaction of (conserved structures of) the non-viable micro-organisms with the immune system, particularly the mucosal immune system. According to a particularly preferred embodiment, the non-viable probiotics are metabolically-active. By "metabolically-active" is meant that they exhibit at least some residual enzyme activity characteristic to that type of probiotic.

By the term "non-viable" as used herein is meant a population of bacteria that is not capable of replicating under any known conditions. However, it is to be understood that due to normal biological variations in a population, a small percentage of the population (i.e. 5% or less) may still be viable and thus capable of replication under suitable growing conditions in a population which is otherwise defined as non-viable.

By the term "viable bacteria" as used herein is meant a population of bacteria that is capable of replicating under suitable conditions under which replication is possible. A population of bacteria that does not fulfil the definition of "non-viable" (as given above) is considered to be "viable".

By the term "bioactive component" as used herein is meant a component which has a physiological effect upon the body when consumed in adequate amounts.

Unless stated otherwise, all percentages mentioned in this document are by weight based on the total weight of the composition.

According to a particularly preferred embodiment, the present edible product comprises at least 50 wt. % of water, fat or a combination of water and fat. Even more preferably, the present edible product comprises at least 70 wt. %, most preferably at least 80 wt. % of water, fat or a combination of water and fat.

The edible product according to the present invention may be a liquid or a spreadable or spoonable product. Preferably the product is a liquid. The edible product may suitably take the form of e.g. a beverage, a spread, a dressing, a dessert or a mayonnaise. Preferably, the edible product is a beverage, a dessert or a spread. More preferably, the edible product is a beverage or a spread, especially a spread in the form of an oil-in-water emulsion. The term "spread" as used herein encompasses spreadable products such as margarine, spreadable cheese based products and processed cheese. Most preferably, the present product is a beverage. Such a beverage typically contains at least 60 wt. % water and 0-20 wt. % of dispersed fat. Preferably, such beverage contains at least 70 wt. % water and 0-10 wt. % of dispersed fat.

The probiotic bacteria used in the product according to the present invention may be any conventional probiotic bacteria. It is preferred that the probiotic bacteria are selected from genera *Bifidobacterium, Propionibacterium, Enterococcus, Streptococcus, Lactococcus, Bacillus, Pediococcus, Micrococcus, Leuconostoc, Weissella, Oenococcus* and *Lactobacillus*, with *Lactobacillus* and *Bifidobacterium* being the most preferred.

Suitable types of probiotic bacteria which may be used include the following bacteria and spores thereof; *Bacillus natto, Bifidobacterium adolescentis, B. animalis, B. breve, B. bifidum, B. infantis, B. lactis, B. longum, B. subtilis, B. cereus, B. licheniformis, B. pumilus, B. clausii, B. coagulans, Enterococcus faecium, Enterococcus faecalis, Escherichia coli, Lactobacillus acidophilus, L. brevis, L. casei, L. delbrueckii, L. fermentum, L. gasseri, L. helveticus, L. johnsonii, L. lactis, L. paracasei, L. plantarum, L. reuteri, L. rhamnosus, L. sakei, L. salivarius, Lactococcus lactis, Lactococcus cremoris, Leuconostoc mesenteroides, Leuconostoc lactis, Pediococcus acidilactici, P. cerevisiae, P. pentosaceus, Propionibacterium freudenreichii, Propionibacterium shermanii, Streptococcus thermophilus* and *Streptococcus salivarius*.

Particular probiotic strains which are suitable according to the present invention are: *Lactobacillus casei shirota, Lactobacillus casei* DN-114 001, *Lactobacillus rhamnosus* GG (ATCC53103), *Lactobacillus reuteri* ATCC55730/SD2112, *Lactobacillus rhamnosus* HN001, *Lactobacillus plantarum* 299v (DSM9843), *Lactobacillus johnsonii* La1 (I-1225 CNCM), *Lactobacillus plantarum* WCFS1, *Lactobacillus helveticus* CP53, *Bifidobacterium lactis* HN019, *Bifidobacterium animalis* DN-173010, *Bifidobacterium animalis* Bb12, *Bifidobacterium longum* BB536, *Lactobacillus casei* 431, *Lactobacillus acidophilus* NCFM, *Lactobacillus reuteri* ING1, *Lactobacillus salivarius* UCC118, *Propionibacterium freudenreichii* JS, *Escherichia coli* Nissle 1917.

The levels of the food grade probiotic bacteria to be used according the present invention will depend upon the types thereof. It is preferred that the present product contains probiotic bacteria in an amount between of between $10^4$ and $10^{10}$, preferably between $5 \times 10^5$ and $10^9$ bacteria per gram.

In accordance with a preferred embodiment of the invention, the probiotic bacteria employed are viable probiotic bacteria. The use of viable probiotic bacteria offers the advantage that these probiotic bacteria may become a part of the intestinal microflora, thereby providing additional health benefits besides those related to the metabolisation of ginseng components.

The present product contains considerable levels of ginseng polysaccharides. These levels clearly exceed the concentrations found in edible product to which ginseng or ginseng extract has been added for flavouring purposes. Preferably, the ginseng polysaccharides are contained in the present product in a concentration of at least 0.8 mg/g, more preferably of at least 1.0 mg/g. Typically, the concentration of ginseng polysaccharides does not exceed 50 mg/g, preferably it does not exceed 25 mg/g.

Many commercially available ginseng extracts that are marketed as being nutritionally beneficial contain significant levels of ginsenosides. As a matter of fact the extraction procedures by which these extracts are obtained have been optimised to produce high yields of ginsenosides. These commercial ginseng extracts contain relatively low levels of ginseng polysaccharides. In contrast, the product according to the present invention preferably contains a ginseng extract in which relatively high levels of ginseng polysaccharides are combined with relatively low levels of ginsenosides. Thus, in a preferred embodiment, the weight ratio ginseng polysaccharides to ginsenosides in the present product exceeds 1:10. More preferably, said ratio exceeds 1:4, even more preferably 1:1, especially 4:1 and most preferably 8:1.

The ginseng polysaccharides in the present product may be derived from various ginseng varieties, such as *Panax quinquefolium, Panax ginseng, Panx notoginseng, Panax trifolia, Panax japonica, Panax pseudoginseng, Panax vietnamensis, Panax elegatior, Panax wangianus, Panax bipinratifidus*. Preferably, the ginseng polysaccharides employed in the present product originate from *Panax*, most preferably from *Panax quinquefolium*.

The ginseng polysaccharides employed in the present product are suitably obtained by an extraction process comprising the subsequent steps of:

combining ginseng with a $C_1$-$C_6$ alcohol at elevated temperatures, e.g. 60-120° C., for at least 30 minutes to produce a first ginseng solution;

separating the first ginseng solution to produce a first ginseng residue and a alcohol-ginseng solution;

combining the first ginseng residue with water at elevated temperatures, e.g. 60-120° C., for at least 30 minutes to produce a ginseng residue solution;

separating the ginseng residue solution to produce a second ginseng residue and an aqueous extract solution containing a ginseng extract; and drying or concentrating the aqueous extract solution.

More detailed information about such an extraction process is provided in U.S. Pat. No. 6,432,454 which is incorporated herein by reference.

The inventors have observed that best results are obtained with ginseng extracts containing relatively large amounts of polysaccharides containing a large number of monosaccharide units. Accordingly, in a preferred embodiment the product contains at least 0.5 mg/g of ginseng polysaccharides with a molecular weight of at least 2,000, preferably of at least 10,000, most preferably of at least 30,000.

In terms of the carbohydrate composition, the preferred ginseng polysaccharides can be characterised as follows:

0.5-8 mol. % rhamnose;
11-49 mol. % galacturonic acid;
2-60 mol. % glucose;
10-33 mol. % galactose; and
11-25 mol. % arabinose, wherein the aforementioned monosaccharides together represent at least 80 mol. %, preferably at least 90 mol. % of all the monosaccharides contained in the ginseng polysaccharides.

The products according to the invention preferably have a pH in the range of 3.8-5.5. According to a particularly preferred embodiment the pH of the product is such that growth of the viable probiotic bacteria contained in the product is effectively inhibited.

Naturally, the present composition may contain further ingredients, including ingredients that have a favourable health impact. Non-limiting examples of additional ingredients that may suitably be incorporated in the present composition are: vitamins, minerals, prebiotics, phytosterols, polyphenols, proteins, fibres, herbs and saponins.

Another aspect of the present invention relates to a packaged edible liquid product comprising a package, one or more edible liquids contained within said package and optionally a conduit, which edible liquid when released from said package through one or more predefined opening or through the optional conduit, yields an edible liquid product as defined herein before. Typically, the present product comprises between 50 and 200 ml of the edible liquid, which amount represents a single serving.

The packaged product may suitably contain a single edible liquid product as defined herein before. Alternatively, the package may contain two different edible liquids, wherein one liquid provides the bulk of the probiotic bacteria and the other liquid provides the bulk of the ginseng polysaccharides. In yet another alternative embodiment, the package contains an edible liquid containing the ginseng polysaccharides, whereas the probiotic bacteria are immobilised in a conduit. The conduit may be an integral part of the package or it may be provided separately. By removing the edible liquid from the package by passing it through said conduit the probiotic bacteria are dispersed into said liquid, thereby yielding an edible liquid product as defined herein before. Naturally in the latter embodiment the ginseng polysaccharides and probiotic bacteria may be swapped, meaning that the polysaccharides are immobilised in the conduit and the probiotics are incorporated in the edible liquid. All of the aforementioned embodiments are encompassed by the present invention.

Yet another aspect of the present invention relates to the combined use of probiotic bacteria and ginseng polysaccharides in therapeutic or prophylactic treatment, said treatment comprising combined oral administration of probiotic bacteria in a daily amount of at least $10^6$ bacteria and ginseng polysaccharides in an amount of at least 50 mg. The aforementioned treatment is particularly effective when applied to mammals, especially humans.

The probiotic bacteria and ginseng polysaccharides may be administered in the form of a single composition containing both components. Alternatively, these components may be administered separately, provided both are administered within a time interval of not more than 5 minutes, preferably of not more than 2 minutes. Preferably, the probiotic bacteria and ginseng polysaccharides are administered in the form of an edible product as defined herein before.

The combined administration of probiotic bacteria and ginseng polysaccharides in accordance with the invention is particularly suitable for restoring or maintaining immune function. A particularly preferred embodiment of the invention relates to the combined use of probiotic bacteria and ginseng polysaccharides in the indicated dosage as part of the treatment or prevention of respiratory and gastrointestinal infections.

In a particularly preferred embodiment the therapeutic or prophylactic use of the combination of probiotic bacteria and ginseng polysaccharides comprises at least once daily oral administration, preferably at least once daily administration of a liquid edible product as defined herein before in an amount of 50-200 ml.

Finally, a further aspect of the present invention relates to a method of producing a packaged edible liquid product as described herein before, said method comprising:

preparing the edible liquid by combining (i) a concentrate containing probiotic bacteria in an amount of at least $10^5$ bacteria with (ii) a ginseng extract and (iii) an aqueous diluent, said aqueous diluent representing at least 50 wt. % of the edible liquid so prepared;

introducing the edible liquid in the package; and closing the package.

The invention is further illustrated by means of the following examples.

EXAMPLES

Example 1

Phagocytosis is an important immune mechanism that protects animals against, amongst others, bacterial and fungal infections. In vitro studies were conducted to assess the combined effect of probiotics and ginseng polysaccharides on phagocytosis.

The following probiotic strains have been used and have been grown under anaerobic conditions for 24 h at 37° C. in 20 ml medium as indicated in Table I:

TABLE I

| nr | Strain | Depot nr | Medium [1] |
|---|---|---|---|
| 1 | *Lactobacillus reuteri* SD2112 | ATCC55730 | MRS |
| 2 | *L. rhamnosus* HN001 | [2] | MRS |
| 3 | *L. plantarum* WCFS1 | NCIMB8826 | MRS |
| 4 | *L. delbrueckii* LMG6891 | LMG6891 | MRS |

[1] MRS (1) and M17 (2) are cultivation media optimised for *Lactobacilli* and *Streptococci/Lactococci*, respectively. (1) Terzaghi, B E, Sandine, W E, (1975) Applied Microbiology 29: 807-813 (2) de Man J. C., Rogosa M. and Sharpe M. E. (1960) Appl. Bact. 23. 130-135.
[2] Also known as DR20. Sold by Danisco, Niebull, Germany (Howaru *Rhamnosus*)

The ginseng extract used is sold under the product name CVT-E002, Cold-Fx by CV Technologies Inc. Calgary, Alberta, Canada. The monosaccharide composition of the carbohydrates contained in the ginseng extract is glucose 50.8%, galacturonic acid 22.8%, galactose 11.9%, arabinose 11.2%, rhamnose 2.85%.

Each grown culture was split in 2 small falcon tubes (A and B) and the cells were centrifuged for 10 minutes at 5000 rpm in an Eppendorf tabletop centrifuge. The supernatant was removed from the centrifuged samples and the remaining pellets were resuspended in 5 ml sterile water and centrifuged again. The pellets of set A were resuspended in a solution of 100 mg ginseng extract in 5 ml water, filter sterilized. The pellets of set B were resuspended in 5 ml sterile water. All samples were incubated for 21 h at 37° C. As a control sample a solution of 100 mg ginseng extract in 5 ml water was used and stored in a refrigerator. A reference sample identical to the control sample was incubated as such. At the end of the incubation cells were centrifuged again for 10 minutes at 5000 rpm. The supernatants were filtered over a 0.2 μ filter to produce ingredient solutions.

Modulation of Phagocytes In Vitro

The test method for modulation of phagocytic activity uses the Phagotest® (Orpegen, Heidelberg, Germany) and is described as follows:

Blood was obtained from healthy human volunteers in sodium heparin tubes. 45 ul of whole blood and 5 ul ingredient solution were incubated for 20 minutes at 37° C. in a shaking water bath before FITC-labelled *E. coli* (ratio 25:1) were added. Control incubations consisted of water or 100 ng/mL lipopolysaccharide (LPS) samples (mean±sd in triplicate). The incubation was stopped after 5 minutes by adding 100 ul ice cold Quench solution. The cells were washed twice by adding 1.5 ml Washbuffer and centrifugation for 5 min at 250 g. By adding 1 ml Lysis solution the erythrocytes were lysed and samples were fixed for 20 minutes. Cells were washed with 1.5 Wash buffer and centrifugation for 5 min at 250 g, and stained with propidium iodide.

Analysis was performed by flowcytometry (Coulter EPICS XL flowcytometer, Beckman Coulter Nederland B V, Mijdrecht). Leukocytes were gated into monocyte and granulocyte populations according to FSC/SSC profile. The percentage of phagocyting cells in these populations and the mean fluorescence of positive granulocytes and monocytes were determined. The phagocytic index is calculated by (percentage phagocytosis X mean fluorescence)/1000. The results were normalized to the effect LPS. The results are shown in FIG. 1. It is clear that the combination of ginseng and microorganisms significantly changes the biological activity on phagocytosis in a favourable manner.

Example 2

Growth of a probiotic strain in a cultivation medium containing different concentrations of ginseng extract (as in example 1)

*Lactobacillus reuteri* SD2112 or *Bifidobacterium lactis* Bb12 (sold by Chr. Hansen, Horsholm, Denmark), were grown under anaerobic conditions for 24 h at 37° C. in respectively 25 ml MRS medium (as in example 1) or MRS medium containing 0.05% cysteine. Each culture was split into 5 ml aliquots (A-E) in small Falcon tubes and centrifuged for 10 minutes at 5000 rpm in an Eppendorf tabletop centrifuge. The supernatant was removed from the centrifuged samples. The *L. reuteri* samples were resuspended in 20 ml MRS medium containing respectively 100 mg ginseng extract (1A), 50 mg ginseng extract (1B), 25 mg ginseng extract (1C), 10 mg ginseng extract (1D) or no ginseng extract (1E). The *B. lactis* samples were resuspended in MRS medium containing 0.05% cysteine and respectively 100 mg ginseng extract (2A), 50 mg ginseng extract (2B), 25 mg ginseng extract (2C), 10 mg ginseng extract (2D) or no ginseng extract (2E). All samples were incubated under aerobic conditions for 24 h at 37° C. Bacterial cell numbers were determined directly after resuspending the cells (T=0) and after 24 h of growth (T=24) by plate counting on MRS medium and incubation for 2 days at 37° C. under anaerobic conditions. The results are depicted in Table II.

TABLE II

| Sample | T = 0 (cells/ml) | T = 24 (cells/ml) |
|--------|------------------|-------------------|
| 1A | $1.1 \times 10^8$ | $8.5 \times 10^8$ |
| 1B | $1.1 \times 10^8$ | $7.4 \times 10^8$ |
| 1C | $1.1 \times 10^8$ | $1.1 \times 10^8$ |
| 1D | $1.1 \times 10^8$ | $6.5 \times 10^8$ |
| 1E | $1.1 \times 10^8$ | $6.0 \times 10^8$ |
| 2A | $2.4 \times 10^8$ | $5.2 \times 10^8$ |
| 2B | $2.4 \times 10^8$ | $5.5 \times 10^8$ |
| 2C | $2.4 \times 10^8$ | $4.7 \times 10^8$ |
| 2D | $2.4 \times 10^8$ | $4.7 \times 10^8$ |
| 2E | $2.4 \times 10^8$ | $5.0 \times 10^8$ |

The results show that ginseng extract, up to a concentration of 100 mg/20 ml does not influence growth of probiotic strains.

Example 3

From Xi Yang Shen powder (*Panax Quinquefolium* root) polysaccharides were extracted as described below. The starting material was sold under the name "Plum Flower Brand" and was manufactured by Lanzhou and Guang Zhou factories (China).

To remove colour and small molecules 25 g of Xi Yang Shen powder was washed 2 times with 200 ml of 85% ethanol in water for 2.5 hours at 80° C. and 1 time with 200 ml of 85% ethanol in water for 1.5 hours at 80° C. After decanting the ethanol/water supernatant the pellet was dried overnight in a fuming cabinet. The polysaccharides were extracted by adding 200 ml milli-Q water and boiled for 3 hours. After centrifugation the pellet was again suspended in 200 ml milli-Q water and boiled for 3 hours. The supernatants of the first and second extraction were collected and lyophilised.

Carbohydrates were quantified according an adapted method of Dubois et al Anal. Chem. 28:380-356 (1956). A calibration curve of 0-240 mg/l glucose was prepared. In a microplate well 50 μl sample, calibration sample or water was added. After the addition of 20 μl resorcinol (6 g/l) and 90 μl $H_2SO_4$ (in fuming cabinet) the plate was gently shaken for 60 seconds. After incubation for 20 minutes at 80° C. the extinction was measured at 450 nm against sample 20 μl with water instead of resorcinol solution. The amount of polysaccharide was calculated via linear regression of the calibration curve with glucose and expressed in relative amount (w/w) polysaccharides per lyophilised sample.

Analysis showed that the polysaccharide content of the lyophilized polysaccharide extract was 80.5%.

The monosaccharide composition of the lyophilized polysaccharide extract was determined using the methodology described below.

Acid hydrolysis of the polysaccharide samples was performed to obtain monosaccharides. Samples of 10 mg/ml were made in 2 M HCl by dissolving freeze dried extract in 1000 μl 18MΩ-water and subsequently 200 μl of 37% HCl was added (pro rata at other weights), the solution was thoroughly mixed on a vortex mixer followed by an incubation of 6 hours at 95° C. in a preheated water bath with cover. During incubation the containers holding the samples were closed to prevent volume loss by evaporation. The samples were transferred to sample vials and centrifuged in an Eppendorf centrifuge at 15600×g for 10 minutes. The supernatants were transferred to tubes and the pH was adjusted to a pH between 3 and 7 with 10 M NaOH (about 200 μl of 10 M NaOH was added to 1200 μl of sample in 2 M HCl), the pH was checked with a piece of universal pH paper. The samples were then filtered (0.45 μm) and put in amber 1 ml HPLC vials with caps (Waters, order nr WAT025053).

The monosaccharide composition of the hydrolysed polysaccharide extract was determined by means of HPLC. An Aminex HPX-87H (300×7.8 mm) HPLC column from Bio-Rad was used for monosaccharide determination. Diluted sulphuric acid (5 mM $H_2SO_4$, pH 2.0) was used as eluent. The flow rate of the HPLC (LC-10AT, Shimadzu) was set on 0.6 ml/min and the column temperature was kept at 65° C. in a column oven (CTO-10AS, Shimadzu). Dual detection of refractive index (RID-10A, Shimadzu) and UV (220 nm and 280 nm, type SPD-10A, Shimadzu) was used. Calibration mix (10 μl) was injected (auto injector SIL-10AD, Shimadzu) after every sixth sample and 5 μl (10 mg/ml) of the polysaccharide samples after acid hydrolysis were injected. The Shimadzu Client/Server (Version 7.3 SP1, build 13) was used as software package to control the HPLC and to evaluate the data. The peak areas of the peaks between 8 and 18 minutes were listed by the software (data not shown) the total peak area was put at 100%. The area of each individual peak was calculated to its share (%) of the total area. The calibration chromatogram of the monosaccharides prior every six samples was used for peak identification of the samples.

The Aminex HPX-87H HPLC column was first calibrated with pure monosaccharide solutions (1 mg/ml) dissolved in 18MΩ-water to determine the retention times, then a mix was made of all monosaccharides. The monosaccharides were all purchased at Sigma-Aldrich. The monosaccharides are listed in Table III. All monosaccharides were well separated on the Aminex HPX-87H HPLC column under the used conditions except for the retention times coded with **, they eluted all as one large peak with the top at 10.93 minutes. The mix used for calibration consisted of the monosaccharides as listed in Table III, 10 μl was injected onto the column.

TABLE III

Monosaccharides used for calibration

| Monosaccharide | Retention time (min) |
| --- | --- |
| D-galacturonic acid sodium salt | 9.68 |
| D-glucose (dextrose monohydrate) | 10.20 |
| D(+)galactose | 10.92** |
| D(+)xylose | 11.01** |
| L-rhamnose monohydrate | 11.59 |
| L(+)arabinose | 11.95 |

Analysis showed that the monosaccharide composition of the hydrolysed polysaccharide extract was as follows (% of total area under peaks):

| | |
| --- | --- |
| galacturonic acid | 11.2% |
| glucose | 79.3% |
| galactose and xylose | 6.5% |
| rhamnose | 1.1% |
| arabinose | 1.9% |

A 20 g/l solution of the lyophilised polysaccharide extract in LAL water from Cambrex™ was made and stirred for 1 hour with a magnetic stirrer. After autoclaving for 15 minutes at 121° C. in an Astell™ autoclave 50 ml was taken for conversion by probiotics as described before in example 1.

The results shown in FIG. 2 clearly show that the combination of ginseng extract and micro-organisms significantly changes the biological activity on phagocytosis in a favourable manner.

The invention claimed is:

1. An edible product comprising:
   (a) probiotic bacteria in an amount of at least $10^3$ bacteria per gram of the product;
   (b) at least 0.5 mg/g of ginseng polysaccharides with a molecular weight of at least 2,000; and
   (c) optionally, ginsenosides,
   wherein the weight ratio of ginseng polysaccharides to ginsenosides exceeds 1:1.

2. The edible product according to claim 1, wherein the probiotic bacteria are selected from one or more of the genera *Lactobacillus, Bifidobacterium, Propionibacterium, Enterococcus, Streptococcus, Lactococcus, Bacillus, Pediococcus, Micrococcus, Leuconostoc, Weisella, Oenococcus* and combinations thereof.

3. The edible product according to claim 1, containing probiotic bacteria in an amount of between $10^4$ and $10^{10}$ bacteria per gram.

4. The edible product according to claim 1, wherein the probiotic bacteria are viable probiotic bacteria.

5. The edible product according to claim 1, containing at least 0.8 mg/g of the ginseng polysaccharides.

6. The edible product according to claim 1, wherein the weight ratio ginseng polysaccharides to ginsenosides exceeds 4:1.

7. The edible product according to claim 1, wherein the ginseng polysaccharides originate from Panax.

8. The edible product according to claim 1, containing at least 0.5 mg/g of ginseng polysaccharides with a molecular weight of at least 10,000.

9. The edible product according to claim 1, further comprising water and/or fat, wherein the water and fat comprise at least 50 wt. % of the edible product.

10. A packaged edible liquid product comprising a package with one or more predefined openings, the package comprising two different liquids that when combined produce an edible product according to claim 1, wherein one of the two different liquids provides a bulk of the probiotic bacteria and the other of the two different liquids provides a bulk of the ginseng polysacharides.

11. A method of producing a packaged edible liquid product according to claim 10, said method comprising:
   (a) combining (i) a concentrate containing probiotic bacteria in an amount of at least $10^5$ bacteria with (ii) a ginseng extract and (iii) an aqueous diluent, said aqueous diluent constituting at least 50 wt.% of the edible product to provide an edible liquid product;
   (b) introducing the edible liquid product in the package; and
   (c) closing the package.

12. The edible product according to claim 1, comprising ginsenosides, wherein the weight ratio of ginseng polysaccharides to ginsenosides exceeds 1:1.

* * * * *